US009222905B2

(12) United States Patent
Valero et al.

(10) Patent No.: US 9,222,905 B2
(45) Date of Patent: Dec. 29, 2015

(54) DEVICE FOR THE SELECTIVE DETECTION OF BENZENE GAS, METHOD OF OBTAINING IT AND DETECTION OF THE GAS THEREWITH

(75) Inventors: Eduard Llobet Valero, Tarragona (ES); Radouane Leghrib, Tarragona (ES); Marc Delgado Olivella, El Prat de Llobregat (ES); Jean-Jacques Pireaux, Jambes (BE); Alexandre Felten, Namur (BE); Jérôme Guillot, Belvaux (LU); Henri-Nöel Migeon, Belvaux (LU); Ali Mansour, Belvaux (LU); François Amand Baudouin Reniers, Watermael-Boitsfort (BE); Nicolas Yves Claessens, Brussels (BE); Frédéric Gilbert Michel Demoisson, Dijon (FR)

(73) Assignees: Universitat Rovira I Virgili, Tarragona (ES); Sensotran, S.L., El Prat de Llobregat (ES); University Of Namur, Namur (BE); Centre de Recherche Public—Gabriel Lippmann, Belvaux (LU); Université Libre de Bruxelles, Brussels (BE)

( * ) Notice: Subject to any disclaimer, the term of this patent is extended or adjusted under 35 U.S.C. 154(b) by 477 days.

(21) Appl. No.: 13/504,274

(22) PCT Filed: Nov. 2, 2010

(86) PCT No.: PCT/IB2010/054957
§ 371 (c)(1),
(2), (4) Date: Jun. 21, 2012

(87) PCT Pub. No.: WO2011/055298
PCT Pub. Date: May 12, 2011

(65) Prior Publication Data
US 2012/0247180 A1    Oct. 4, 2012

(30) Foreign Application Priority Data

Nov. 9, 2009  (ES) .................................. 200930969

(51) Int. Cl.
G01N 27/00    (2006.01)
G01N 27/12    (2006.01)
B82Y 15/00    (2011.01)

(52) U.S. Cl.
CPC .............. *G01N 27/127* (2013.01); *B82Y 15/00* (2013.01)

(58) Field of Classification Search
CPC .................................................... G01N 27/127
See application file for complete search history.

(56) References Cited

U.S. PATENT DOCUMENTS 7,276,266 B1 *   10/2007  Khare et al. ................... 427/533
2007/0117213 A1 *  5/2007  Cole et al. ..................... 436/146

OTHER PUBLICATIONS

Stussi, Elisa, "International Search Report" for PCT/IB2010/054957, as mailed Mar. 15, 2011, 4 pages.

(Continued)

*Primary Examiner* — Laura Martin
*Assistant Examiner* — Alex Devito
(74) *Attorney, Agent, or Firm* — Winstead PC

(57) ABSTRACT

Device for the selective detection of benzene gas, which comprises, on a base substrate, a combination of at least one functionalized multi- or single-wall carbon nanotube sensor decorated with rhodium clusters, and at least one functionalized multi- or single-wall carbon nanotube sensor decorated with metal clusters selected from gold, palladium, nickel and titanium, and/or undecorated, where said substrate additionally comprises means for measuring the variation in the resistance of said sensors. The device is useful at ambient temperature in the presence or absence of oxygen and easy to handle. It also relates to a method for the manufacturing thereof and for detecting the gas in the chemical industry, the petrochemical industry, petrol stations, or household, aeronautical or research applications.

8 Claims, 10 Drawing Sheets

(56) References Cited

OTHER PUBLICATIONS

Star, A., et al., "Gas Sensor Array Based on Metal-Decorated Carbon Nanotubes", Journal of Physical Chemistry B, vol. 110, Apr. 10, 2006, pp. 21014-21020.

Lu, Y., et al., "A carbon nanotube sensor array for sensitive gas discrimination using principal component analysis", Journal of Electroanalytical Chemistry and interfacialelectro Chemistry, vol. 593, No. 1-2, Aug. 1, 2006, pp. 105-110.

Leghrib, R., et al., "Room-temperature, selective detection of benzene at trace levels using plasma-treated metal-decorated multiwalled carbon nanotubes", Carbon, vol. 48, No. 12, Oct. 1, 2010, pp. 3477-3484.

Zhang, W., et al., "Carbon Nanotubes as Active Components for Gas Sensors", Journal of Sensors, vol. 2009, 2009, pp. 1-16.

Penza, M., et al., "Metal-modified and vertically aligned carbon nanotube sensors array for landfill gas monitoring applications", Nanotechnology, vol. 21, No. 10, Mar. 12, 2010, pp. 1-14.

Leghrib, R., et al., "Selective detection of benzene traces at room temperature using metal decorated carbon nanotubes", Procedia Engineering, vol. 5, Jan. 1, 2010, pp. 385-388.

* cited by examiner

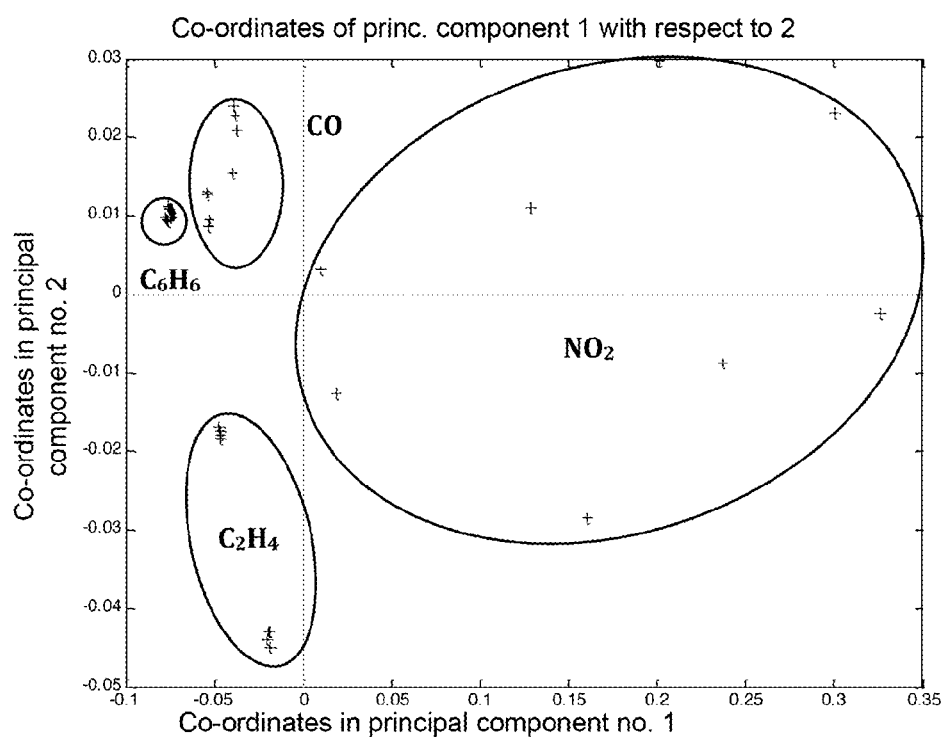

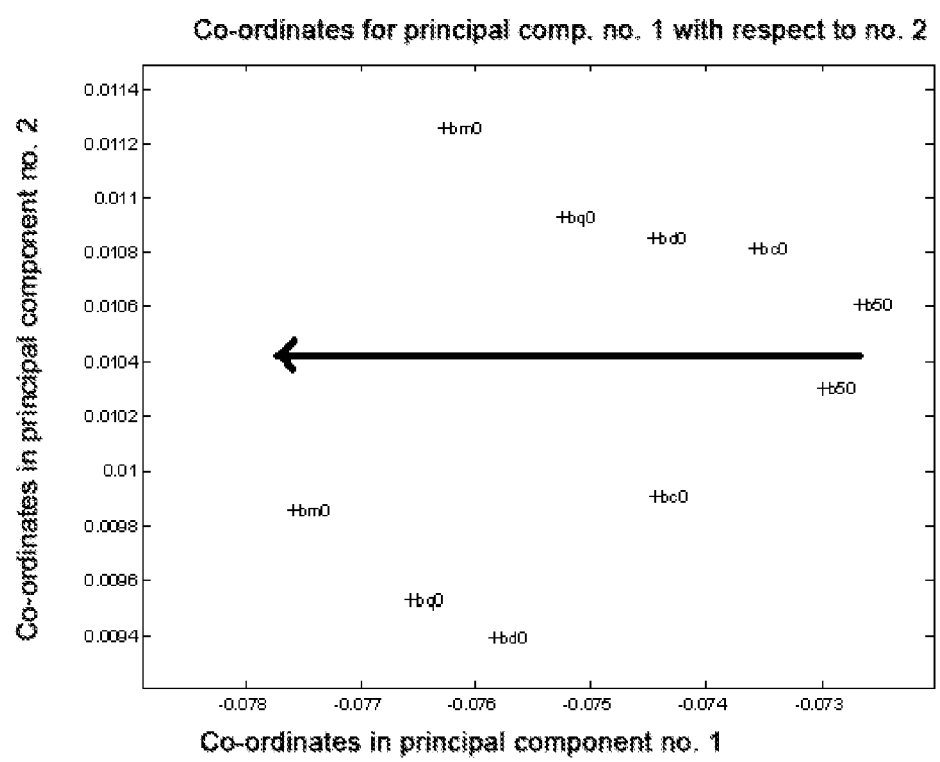

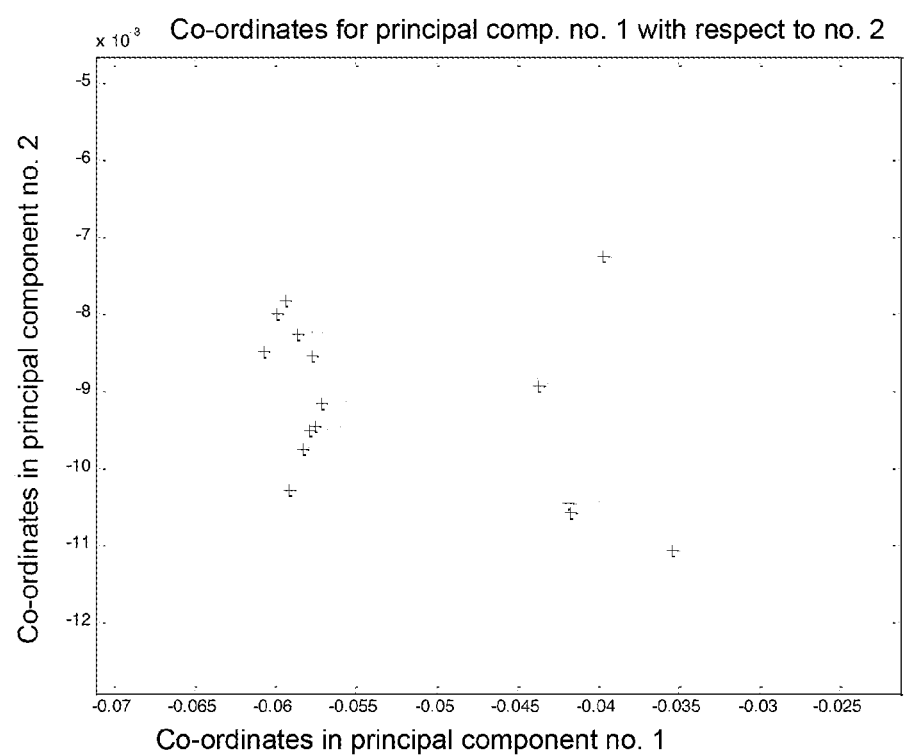

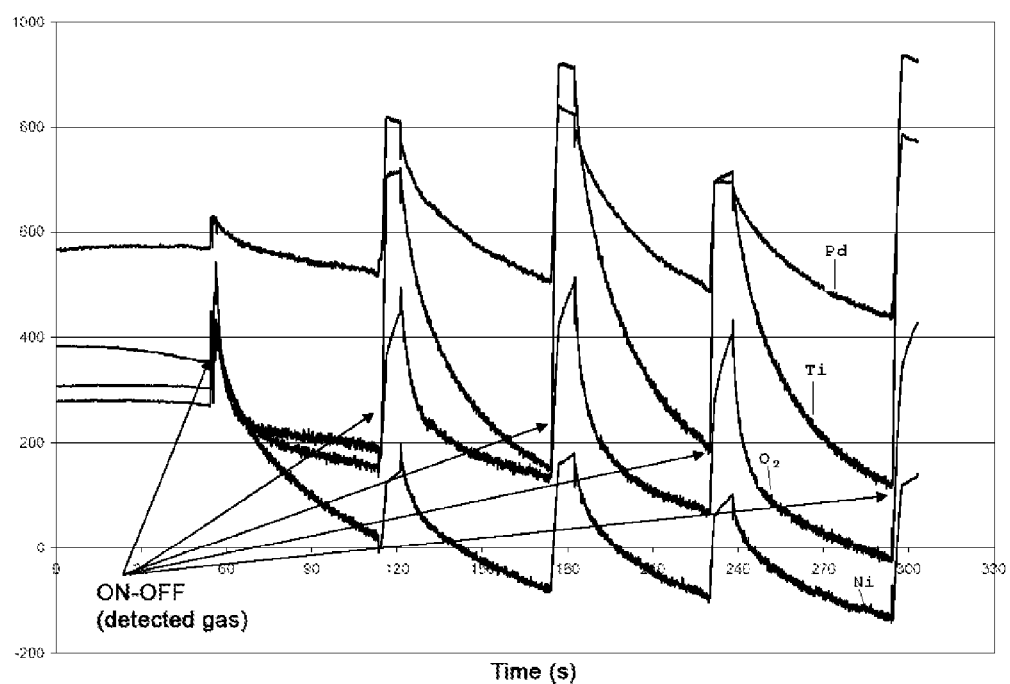

DEVICE FOR THE SELECTIVE DETECTION OF BENZENE GAS, METHOD OF OBTAINING IT AND DETECTION OF THE GAS THEREWITH

FIELD OF THE INVENTION

The object of this invention is to provide a device for the selective detection of benzene gas with a sensitivity in the range of ppb. In particular, the invention provides a device for the detection of benzene gas that is useful at ambient temperature in the presence or absence of oxygen and easy to handle.

The invention also provides a method of obtaining or manufacturing said device, as well as a method of detecting benzene gas in an environment where it is susceptible to being present, such as, for example, the chemical industry, the petrochemical industry, petrol stations, or household, aeronautical or research applications, in the presence of other interfering gases.

BACKGROUND OF THE INVENTION

In the state of the art, there are different devices for the detection of benzene gas based on photoionisation detectors (PIDs). However, these devices are not completely selective toward benzene, since they present sensitivity toward other gases and other volatile organic compounds (VOCs). However, the detection limit for benzene is not less than 100 ppb. Moreover, said devices do not present selectivity toward benzene at concentrations of a few ppb when other interfering gases are present, as may occur, for example, in the petrochemical industry.

On the other hand, devices have been disclosed which are based on retention tubes that retain different gases with the exception of benzene. However, once again, the detection limit of benzene gas is 100 ppb and a new retention device must be used for each analysis.

Devices have also been disclosed for the detection of benzene based on optical analysis, which use a large number of chips as chemical sensors. Each of these chips contains 10 capillaries or measurement channels, which are filled with a specific reagent of the substance to be analysed. These reagents change colour in the presence of the substance to be detected and the intensity of the change in colour provides information about the concentration thereof. However, these devices have a high cost due to the reagents used and, furthermore, only detect benzene gas in a reliable manner when the latter is present at concentrations in the order of 200 ppb or greater.

Laboratory-scale assays have also been performed to detect benzene gas at lower concentrations, using 10.6-eV UV lamps for the ionisation, but a device has still not been found which selectively detects benzene at an industrial scale operating at ambient temperature, in the presence or absence of oxygen and in environments wherein other interfering gases are also present.

In terms of yield, the devices available in the market may be applied to detect benzene in the range 0-200 ppm, with a precision of 50 ppb. However, these devices still use retention tubes, with the disadvantages mentioned above.

On the other hand, benzene sensors based on carbon nanotubes have also been disclosed. However, the proposed sensors exhibit low sensitivity toward benzene when the latter is in the presence of other components, such as interfering gases. Moreover, the sensors based on carbon nanotubes disclosed only detect concentrations in the order of ppm.

It is worth noting that the devices disclosed are either not reversible and, therefore, a new device must be used for each analysis or measurement, or they have a very low response reversibility after being used for the detection of benzene.

Consequently, as yet there is no device for the selective detection of benzene gas within the range of only a few ppb, which is re-usable for different measurements, operates at ambient temperature and in the presence or absence of oxygen.

Benzene sensors based on metal oxides have also been disclosed in the state of the art, in particular, using gold-doped tin oxide. However, the problems associated with metal oxides are a low selectivity (the sensor responds not only to benzene, but also strongly to CO and $NO_2$, amongst others); they must operate at high temperatures, between 350° C. and 400° C., for a reliable, safe detection of benzene; temporary response drifts associated with changes in the structure of the active layer; and degradation of the electrodes due to the high operating temperatures; in addition to a negative effect on the response of said sensors due to the presence of humidity in the environment to be analysed.

Consequently, as yet there is no sensing device in the state of the art for the detection of benzene gas that presents high sensitivity and selectivity in the order of ppb, which may take measurements at ambient temperature, with the energy savings that this entails, and with greater durability, since degradation of the electrodes caused by use at high temperatures is prevented. Moreover, in the state of the art there is no device with high selectivity toward benzene in the presence of other interfering gases, such as, for example, hydrocarbons such as $C_2H_4$, nitrogen oxide, carbon monoxide, amongst the most common. There also are no devices in the state of the art for the detection of benzene gas that are re-usable and maintain the sensitivity and the selectivity during several analyses or measurements.

SUMMARY DESCRIPTION OF THE INVENTION

In accordance with the first aspect of the invention, a device is provided to detect benzene gas in a selective manner, which comprises a combination of sensors the active layers whereof are composed of multi- or single-wall carbon nanotubes, decorated or not with certain metal clusters.

A second aspect of the invention is to provide a method of obtaining or manufacturing said device.

A third aspect of the invention is to provide a method of detecting benzene gas in the presence of other interfering gases at ambient temperature.

A fourth aspect of the invention also relates to the use of the device in accordance with the first aspect of the invention in the selective detection of benzene gas in the chemical industry, the petrochemical industry, petrol stations, or household, aeronautical or research applications.

DESCRIPTION OF THE FIGURES

FIG. 1A is a graph that shows the results of a PCA analysis (principal component analysis) with the response of a combination of 4 carbon nanotube sensors functionalised with oxygen and decorated with rhodium, platinum, and not decorated with metal clusters. The Y-axis shows the co-ordinates of the measurements made on principal component number 2 and the X-axis shows the co-ordinates of principal component number 1. FIG. 1B is an enlargement of FIG. 1A in the benzene area. The arrow indicates increasing concentrations of benzene.

FIG. 2B is an enlargement of FIG. 2A in the benzene area.

FIG. 7 shows repeated experiments of the effect of the desorption of benzene gas from the functionalised carbon nanotubes decorated with Ti, Ni, Pd, or undecorated but functionalised with oxygen plasma ($O_2$).

DETAILED DESCRIPTION OF THE INVENTION

Figure 2A:
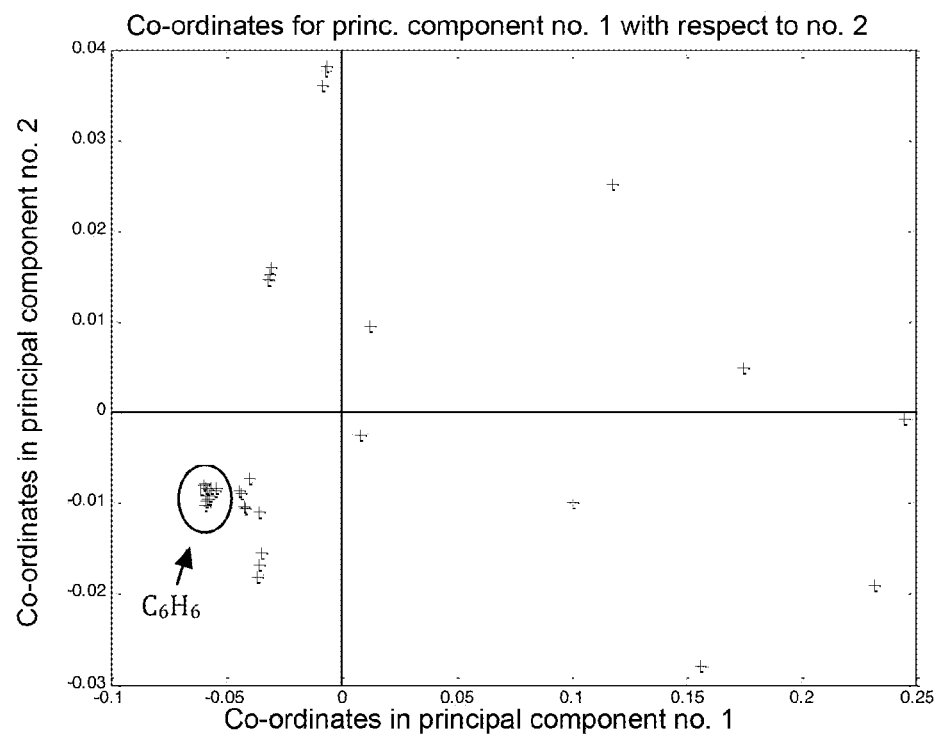
FIG. 2A is a graph that shows the results of a PCA analysis with the response of a combination of 4 carbon nanotube sensors functionalised with oxygen and decorated with rhodium and not decorated with metal clusters. The Y-axis shows the co-ordinates of the measurements made on principal component number 2 and the X-axis shows the co-ordinates on principal component number 1.

A first aspect of the invention provides a device for the selective detection of benzene gas, characterised in that it comprises, on a base substrate, a combination of:

a) at least one functionalised multi- or single-wall carbon nanotube sensor (MWCNT or SWCNT) decorated with rhodium (Rh) clusters, and b) at least one functionalised multi- or single-wall carbon nanotube sensor decorated with metal clusters selected from gold, palladium, nickel and titanium, or undecorated, or mixtures thereof;

where said base substrate additionally comprises means for measuring measure the variation in the resistance of said sensors.

Surprisingly, the combination of sensors in accordance with the first aspect of the invention provides a device that allows for the selective detection of benzene gas in the presence of other interfering gases.

Advantageously, the addition of at least one functionalised multi- or single-wall carbon nanotube sensor decorated with platinum (Pt) clusters makes it possible to determine the concentration of benzene gas present in the environment analysed. For more details, see FIG. 1.

Thus, the combination of sensors in the device described above provides an excellent sensitivity and selectivity toward benzene gas at ppb levels. In particular, the authors of the invention have found that the detection threshold is below 50 ppb, and it may detect concentrations of 10, 20, 30 ppb. Advantageously, the defined device exhibits excellent selectivity toward possible interfering gases, such as hydrocarbons, nitrogen oxide, carbon monoxide, amongst others, as may be verified in the figures and embodiments that follow. Therefore, the invention makes it possible to overcome the low sensitivity and low selectivity problems of the devices designed for the detection of benzene described thus far.

In a preferred embodiment of the invention, the device for the selective detection of benzene gas is characterised in that it comprises a combination of sensors that consists of:

a) at least one functionalised multi- or single-wall carbon nanotube sensor decorated with rhodium (Rh) clusters, b) at least one functionalised multi- or single-wall carbon nanotube sensor decorated with metals clusters selected from gold, palladium, nickel and titanium, and/or undecorated, and c) at least one functionalised multi- or single-wall carbon nanotube sensor decorated with platinum (Pt) clusters.

In yet another preferred embodiment, the device for the selective detection of benzene gas is characterised in that it comprises a combination of sensors that consists of:

a) at least one functionalised multi- or single-wall carbon nanotube sensor decorated with rhodium (Rh) clusters, b) at least one functionalised, undecorated multi- or single-wall carbon nanotube sensor, and c) at least one functionalised multi- or single-wall carbon nanotube sensor decorated with platinum (Pt) clusters.

Preferably, said nanotubes are functionalised in an oxygen plasma.

Thus, a device with a combination of, for example, 4 sensors: Rh, Pt and others decorated with gold, palladium, nickel or titanium, and/or undecorated, is sufficient to detect and quantify benzene gas. It is evident that a combination with a larger number of sensors (6, 8, 10, 12, etc.) will also be useful in accordance with the object of the invention.

Preferably, the means for measuring the variation in the resistance produced in the sensors due to the adsorption of gases on the surface of the functionalised carbon nanotubes are interdigitated metal electrodes. The preferred electrodes are made of gold or platinum.

The base substrate comprises said interdigitated metal electrodes, and a ceramic or silicon base substrate is preferred.

Advantageously, the device may additionally comprise means to cast UV light or to increase the temperature of the sensors that make up the device, so as to perform the desorption of the gases from the surface of the carbon nanotubes that has taken place during the measurement-taking (gas analysis) and thus leave the sensor in a suitable condition for a new analysis. Therefore, the device of the invention is not only single-use, with the advantages that this entails from an economic and an environmental standpoint.

The device may additionally comprise a signal processing module. Likewise, it may also comprise other elements related to electronics and data processing known to those skilled in the art, such as microcontroller-based electronics to acquire the signals from the sensors and implement pattern recognition techniques, such as PCA, and regression models to determine the presence or absence of benzene gas and quantify it within the ppb-ppm range.

Advantageously, the multi- or single-wall carbon nanotubes that make up each sensor are functionalised in a cold plasma. It is well-known that functionalisation of multi- or single-wall carbon nanotubes makes it possible to activate the surface of the (multi- or single-wall) carbon nanotubes and thereby create defects on the surface thereof, where the metal clusters will be homogeneously deposited. A method of functionalising multi- or single-wall carbon nanotubes, and a specific method of depositing the metal clusters on the surface of the nanotubes are not a part of this invention.

Thus, in accordance with the device described above, the functionalised multi- or single-wall carbon nanotubes may be prepared by any known functionalisation technique, although the cold plasma functionalisation technique is preferred. Therefore, in a preferred embodiment of the invention, the device used for the detection of benzene gas in accordance with the first aspect of the invention comprises multi- or single-wall carbon nanotubes functionalised in a cold plasma and decorated or not with metal clusters.

Therefore, a device is provided for the selective detection of benzene gas which is re-usable, economical, and which allows for the quantification of the concentration of benzene gas present in the environment analysed.

A second aspect of the invention provides a method of obtaining or manufacturing a device as defined above, characterised in that the sensors that make it up are prepared in accordance with the following steps:

i) preparation of a dispersion of an organic solution of multi- or single-wall carbon nanotubes, ii) treatment of said dispersion in an ultrasound bath, iii) deposition on the base substrate of said dispersion treated in step ii) by aerographic spraying, iv) annealment of the substrate in order to fix the deposited carbon nanotubes, v) functionalisation of said carbon nanotubes in a reactor by treatment with oxygen plasma, and vi) optionally, decoration of the functionalised carbon nanotubes with the metal clusters by thermal evaporation, cracking of organometallics or colloidal suspension spraying.

Preferably, said organic solution is prepared with an aprotic organic solvent, preferably dimethylformamide or acetone, and the carbon nanotubes are in the form of powder. In this invention, the term "aprotic organic solvent" is understood to be a solvent that is not capable of exchanging protons with the reactants, such as, for example, those belonging to the families of aromatic hydrocarbons, amides, halogenated hydrocarbons, ketones, esters, ethers or sulfones.

Advantageously, the metal clusters are selected from rhodium, platinum, palladium, nickel, gold and titanium.

The method of obtaining the device described above makes it possible to overcome the problems in the prior art related to the loss or migration of the clusters decorated on the multi- or single-wall carbon nanotubes that occurred during manufacturing of the sensor. Using the method of the invention, the thermal annealing treatment is performed prior to decorating the carbon nanotubes with metal clusters.

Advantageously, the order of the steps and the use of an ultrasound treatment step for the dispersion and an annealing or thermal treatment step when the carbon nanotubes have still not been decorated with the corresponding metal clusters prevents, but substantially reduces, the loss or migration of the metal clusters from the surface of the carbon nanotubes.

The method of obtaining or manufacturing a sensing device for the selective detection of benzene gas in accordance with the invention makes it possible to obtain a device with better sensing properties and, therefore, a sensing device with a high reliability.

In accordance with the method of manufacturing the device of the invention, in step vi) masks will be used in order to direct the metal clusters toward the desired areas. Each sensor is formed by multi- or single-wall carbon nanotubes that are functionalised and, optionally, decorated with clusters of a single metal selected from those mentioned above.

Advantageously, the method of obtaining the device which comprises a combination of different types of sensors provides a device with a high stability (loss or migration of the clusters is prevented), non-degradation of the electrodes, since the device of the invention operates at ambient temperature, unlike the temperature used in the sensors disclosed in the state of the art, which ranges between 350° C. and 400° C., and excellent sensitivity toward the presence of interfering gases.

A third aspect of the invention provides a method of selectively detecting the presence of benzene gas using the device defined above, characterised in that it comprises:

taking measurements of the electrical resistance of the functionalised multi- or single-wall carbon nanotube sensors a) and b), and optionally c), which varies in response to the presence of benzene gas, analysing said electrical resistance in order to determine and, optionally, quantify the presence of benzene gas, and when taking a new measurement, applying a source of ultraviolet light to the sensor for a short period of time, or increasing the sensor temperature between 50° C. and 200° C. in order to desorb the gases from the sensor and leave the latter in a suitable condition for a new measurement.

Preferably, desorption of the gases from the sensor is performed by applying a source of ultraviolet light for a short period of time, for example 30, 60 or 90 seconds. Said method of desorbing the gases makes it possible to significantly reduce the sensor's recovery time. Optionally, the desorption may also be performed by increasing the sensor temperature, preferably between 100° C. and 160° C., even more preferably 150° C.

Advantageously, the measurements of benzene gas are performed at ambient temperature. Therefore, the device of the invention makes it possible to overcome the problems in the prior art related to the degradation of the electrodes in the device due to the high temperatures required for the correct operation thereof.

Also advantageously, the device of the invention may operate in the presence or absence of oxygen. It is worth noting that most existing devices for the detection of benzene disclosed in the state of the art can only operate in the presence of oxygen, since the latter participates in the regeneration of the oxide layer when taking a new measurement. Using the device of the invention, the presence or absence of oxygen does not affect the measurement-taking or the regeneration of the sensor for taking a new measurement.

Another aspect of the invention relates to the use of said device to selectively detect benzene gas at concentrations below 100 ppb in the presence of other interfering gases and in the absence or presence of oxygen at ambient temperature. In a preferred embodiment, the device is used in the absence of oxygen. Therefore, the device of the invention has applications in the chemical industry, the petrochemical industry, petrol stations, or household, aeronautical or research applications, or any other environment susceptible to having the existence of benzene gas analysed.

EMBODIMENTS OF THE INVENTION

A device was prepared with a combination of 4 multi-wall carbon nanotube sensors (MWNTC) decorated with rhodium and platinum clusters, and undecorated multi-wall carbon nanotubes. They had all been functionalised with oxygen plasma.

The effect provided by said combination was two-fold. On the one hand, it was possible to discriminate between benzene and potential interfering gases (achievement of a selective benzene detector), as may be observed in FIG. 1A.

Various concentrations of nitrogen dioxide (6, 30, 50, 100 ppm), ethylene (3, 7, 15, 30 ppm), carbon monoxide (2, 5, 10 and 20 ppm) and benzene (50, 100, 200, 500 and 1,000 ppb) were measured. The benzene concentrations were deliberately low as compared to those of the other interfering gases. The PCA analysis (also called score diagram) shown in FIG. 1A demonstrated that, using the multi-sensor device, the different gases measured may be identified and, in particular, benzene may be discriminated.

An enlargement of FIG. 1A centred on the benzene measurement area showed the second effect of said device, i.e. that it was not only possible to discriminate benzene from the other gases, but it was also possible to determine the concentration thereof. See FIG. 1B for more details. In fact, the measurements corresponding to the increasing concentrations of benzene are located from right to left, in a manner quite aligned with principal component number 1 (X-axis). This showed that a linear correlation may be established between the response of the sensors and the concentration of benzene (for example, by means of a partial least squares, PLS, calibration model). Moreover, it was very relevant to find that the increasing concentrations of benzene align with the first principal component, since the latter explains over 90% of the measurement variance. Therefore, the combination of sensors in the device of the invention allows for the selective, quantitative detection of benzene gas in the presence of interfering gases.

Subsequently, a device was assayed wherein the platinum sensor had been suppressed. See FIG. 2A. A combination of 4 carbon nanotube sensors functionalised with oxygen and decorated with rhodium, and not decorated with metal clusters, was prepared. It was observed that, in the absence of platinum, the device of the invention was still capable of discriminating benzene from the other gases. However, in the absence of platinum, it was not possible to measure the different concentrations of benzene. See FIG. 2B, where the measurements are not aligned in accordance with the concentration of benzene at different concentrations (50, 100, 200, 500 and 1,000 ppb). Therefore, it is not possible to quantify benzene in the absence of platinum.

Figure 3A:
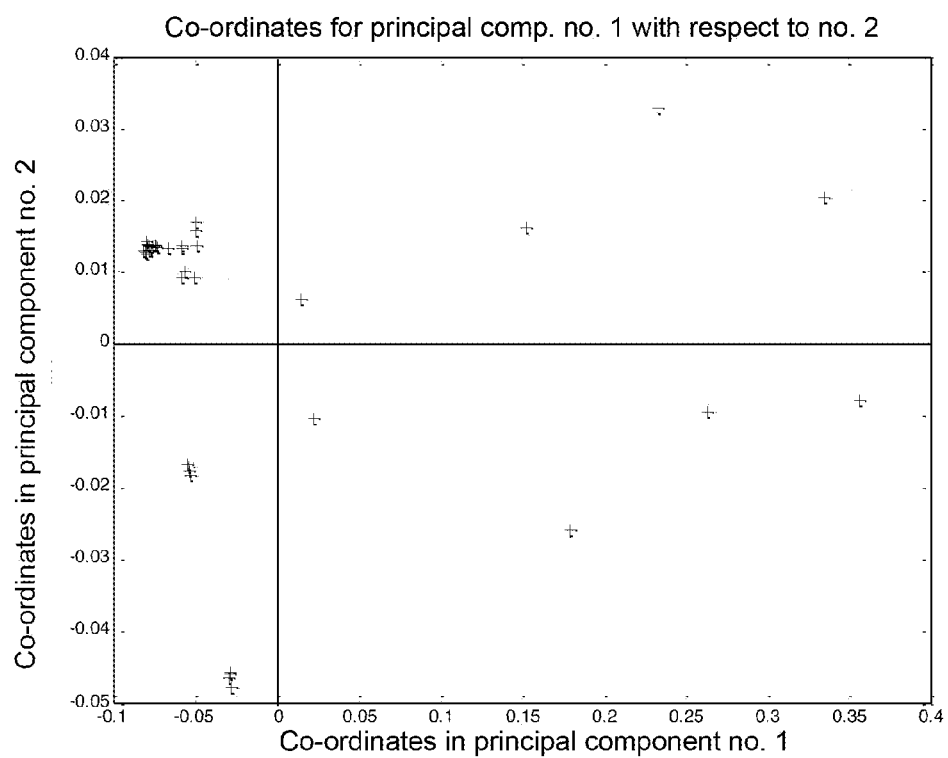
FIG. 3A is a graph that shows the results of a PCA analysis with the response of a combination of 4 carbon nanotube sensors functionalised with oxygen and decorated with rhodium, platinum and palladium. The Y-axis shows the co-ordinates of the measurements made on principal component number 2 and the X-axis shows the co-ordinates on principal component number 1.
Figure 3B:
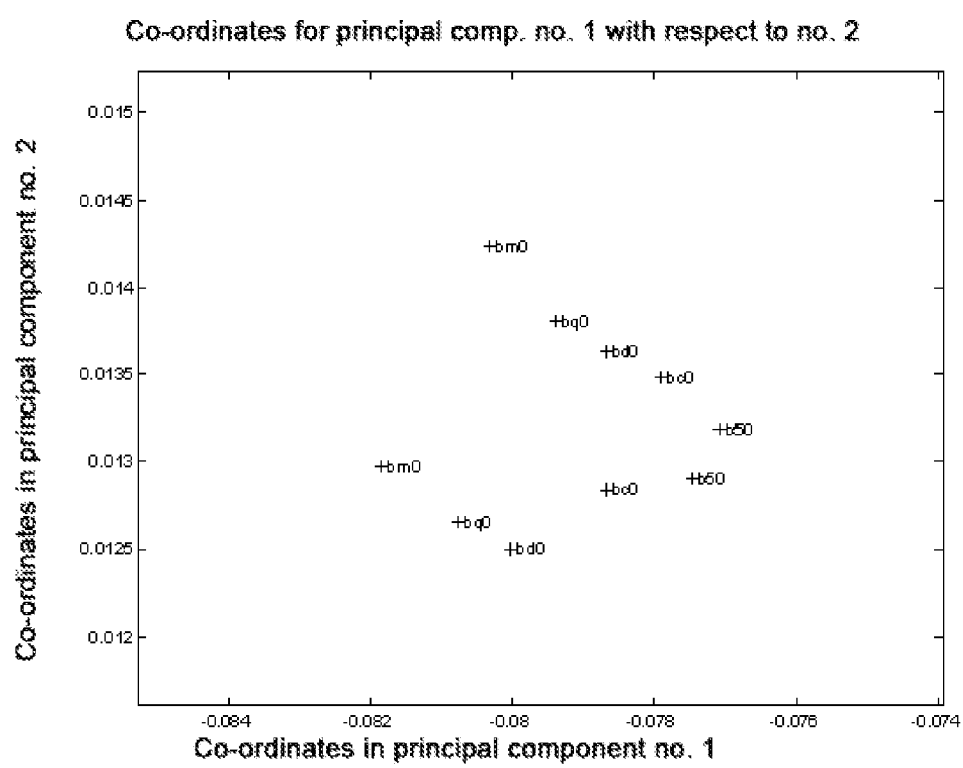
FIG. 3B is an enlargement of FIG. 3A in the benzene area.
Figure 4:
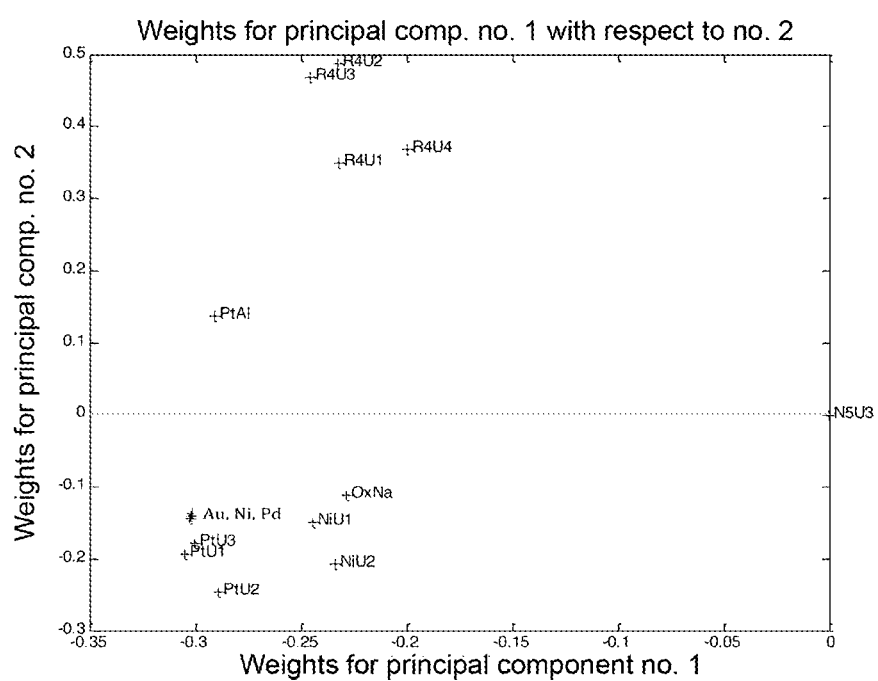
FIG. 4 is a graph that shows the results of a PCA analysis with the response of a combination of 15 functionalised carbon nanotube sensors decorated with rhodium, platinum, palladium, gold and nickel clusters, and not decorated with metal clusters. The different references to said metals, such as NiU1 and NiU2, provide information about the metals that decorate the nanotubes (for example, Ni indicates nickel, R indicates rhodium, Pt indicates platinum, Ox indicates undecorated nanotubes) and to the methods used to decorate the nanotubes (U indicates cracking of organometallics, Na indicates evaporation and Al indicates colloidal suspension spraying). The Y-axis shows the weights of said sensors for principal component number 2 and the X-axis shows the weights for principal component number 1.

A device was also prepared with a combination of 4 carbon nanotube sensors functionalised with oxygen and decorated with rhodium, platinum and palladium, in order to determine the effect of the substitution of a sensor based on carbon nanotubes that was not decorated with metal clusters as compared to the effect of a sensor based on carbon nanotubes decorated with palladium. See FIGS. 3A and 3B. It was observed that said substitution did not modify the sensitivity or the selectivity toward benzene, and it was concluded that both types of sensors have an equivalent function in the device, i.e. both sensors are insensitive toward benzene gas, which, in combination with a sensor that is sensitive to benzene gas (Rh), provided a device with high selectivity toward said gas.

The equivalence between sensors was determined by means of a PCA analysis of a combination of 15 functionalised carbon nanotube sensors decorated with rhodium, platinum, palladium, gold and nickel clusters, and not decorated with metal clusters. The proximity in the values of the weights for the sensors containing gold (Au), nickel (Ni) and palladium (Pd) showed that said metals may be substituted or combined with one another, providing the same function to the device, i.e. reduced or null sensitivity toward benzene gas. Therefore, the functionalised multi- or single-wall carbon nanotube sensors decorated with metal clusters selected from gold, palladium, nickel and titanium provide a response equivalent to that provided by functionalised, undecorated multi- or single-wall carbon nanotube sensors, or a mixture thereof, due to the fact that all of these sensors are insensitive toward benzene gas. It was concluded that these sensors may be substituted by others the PCA analysis whereof provides a response in the same area or very close to it, which will also mean that these sensors are not sensitive toward benzene gas.

Figure 5:
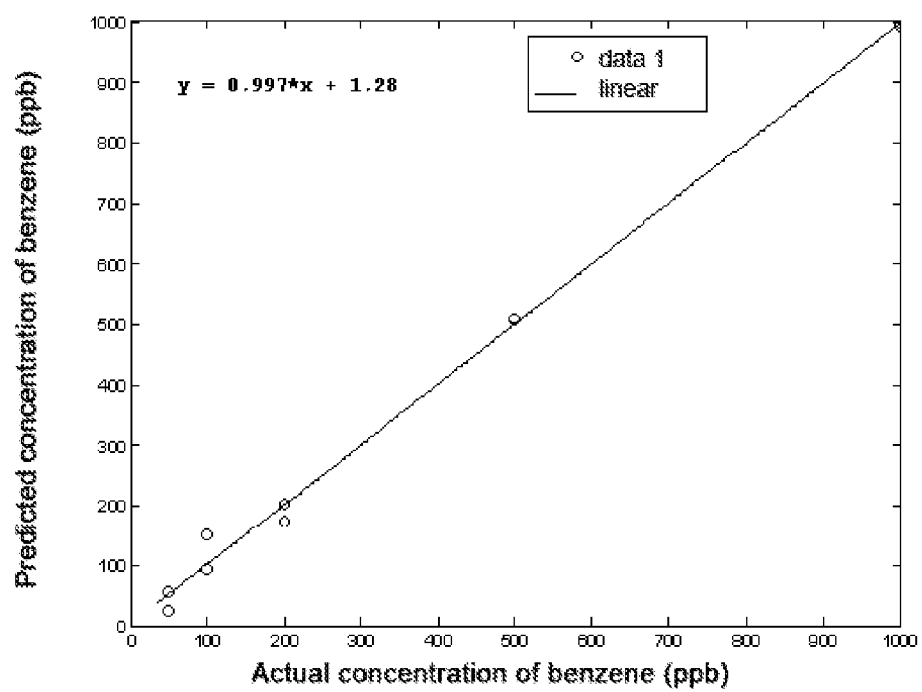
FIG. 5 shows the results obtained for the prediction of the concentration of benzene gas using a PLS calibration model the inputs whereof are the responses of the sensors based on carbon nanotubes decorated with clusters of the metals described for the purpose of the invention. The Y-axis shows the concentration of benzene predicted, in ppb, and the X-axis shows the actual concentration of benzene, in ppb.

A combination was also assayed which included sensors containing rhodium and palladium clusters, in order to determine the concentration of benzene gas. A calibration model was built based on the partial least squares technique (PLS). To this end, ten available measurements from 5 different concentrations of benzene were used. The results obtained using the PLS model are shown in FIG. 5. Said figure shows an excellent linear adjustment between the real and predicted concentration values (the slope of the adjustment is close to 1, the ordinate at the origin is close to 0 and the correlation coefficient of the adjustment is close to 1 (correlation coefficient of the linear regression=0.9986).

Figure 6:
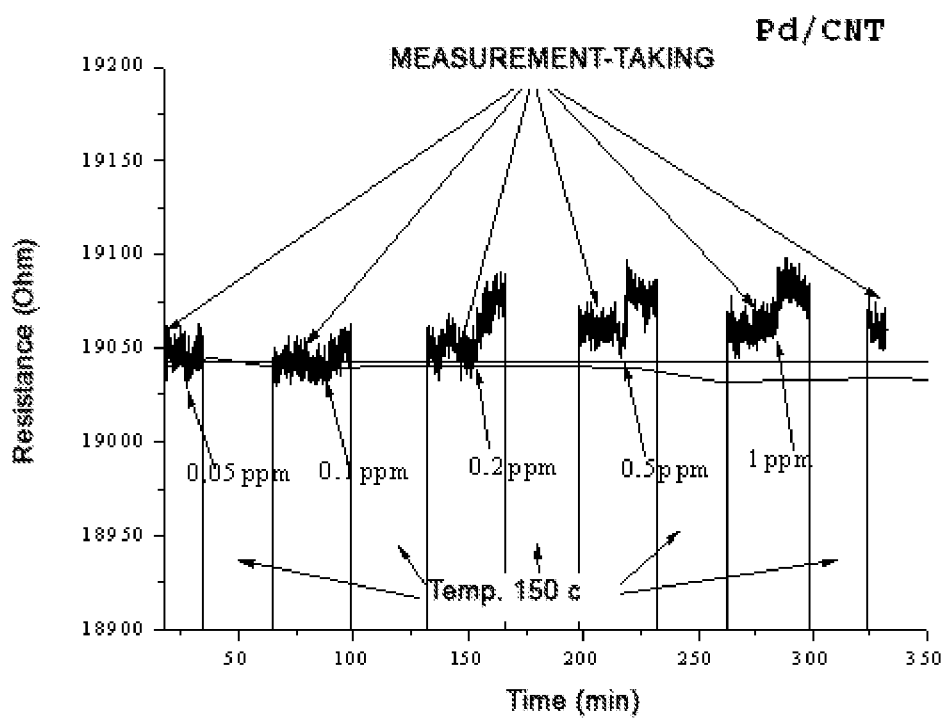
FIG. 6 shows the detection of increasing concentrations of benzene gas using a sensing device in accordance with the invention that comprises, in addition to sensors based on functionalised carbon nanotubes decorated with Rh and Pt, functionalised carbon nanotubes decorated with palladium (Pd/CNT), with the different intervals that indicate the device's regeneration time.

Finally, the device was regenerated, in order to leave it in an optimal condition for the following measurement. See FIG. 6, where it may be observed that, following each measurement, it was heated to 150° C. in order to desorb the gases and, subsequently, new measurements were taken, and so on, up to a total of 5 measurements, with equal sensitivity and selectivity (see the different intervals that indicate the device's regeneration time).

Advantageously, regeneration of the device is performed by applying ultraviolet light to the sensors that contain the benzene gas adsorbed on the surface thereof. See FIG. 7, which shows repeated experiments, and where it may be observed that the regeneration times are within an interval of 60 seconds.

Therefore, the device of the invention is useful in the chemical industry, the petrochemical industry and petrol stations. It is also useful as a personal safety device to protect the staff in the above-mentioned industries that work in environments wherein benzene leaks may occur. It is worth noting that, using the device of the invention measurements may be taken in tanks, pipes or other closed environments even in the absence of oxygen.

It is concluded that, with device of the invention, the following advantages are surprisingly obtained: Excellent sensitivity, which makes it possible to detect benzene at ppb levels. The detection threshold is below 50 ppb. The detection is performed at ambient temperature, with the consequent advantages of energy savings and stability of the active layer and non-degradation of the electrodes. Excellent selectivity toward possible interfering gases, such as hydrocarbons (e.g. $C_2H_4$), nitrogen oxide, carbon monoxide, as shown by the PCA analyses. Possibility of performing a quantitative analysis of the benzene, as shown by the results of the PLS model. Adequate response and recovery times for sensors based on carbon nanotubes.

The invention claimed is:

1. A device for selective detection of benzene gas, the device comprising, on a base substrate, a combination of sensors, the combination of sensors comprising:
   a) at least one multi- or single-wall carbon nanotube sensor functionalized with oxygen plasma and decorated with rhodium (Rh) clusters;
   b) at least one multi- or single-wall carbon nanotube sensor functionalized with oxygen plasma, the at least one sensor being one of undecorated or decorated with metal clusters selected from one of gold, palladium, nickel, and titanium;
   c) at least one multi- or single-wall carbon nanotube sensor functionalized with oxygen plasma and decorated with platinum (Pt) clusters;
   where said base substrate further comprises interdigitated metal electrodes for measuring variation in a resistance of said sensors; and
   wherein said device selectively detects and quantifies benzene gas at a concentration below 100 parts per billion (ppb) in the presence of other interfering gases.

2. The device according to claim 1, wherein said base substrate further comprises means for desorbing the gases from the sensor, such as applying ultraviolet light or heat to the sensor.

3. The device according to claim 1, wherein said interdigitated metal electrodes are preferably made of gold or platinum.

4. The device according to claim 1, wherein said base substrate is made of ceramic material or silicon.

5. The device according to claim 1, wherein the device comprises a signal processing module.

6. Method of using a device according to claim 1, in order to selectively detect and quantify benzene gas at concentrations below 100 ppb in the presence of other interfering gases, the method comprising:
   exposing the device to an environment that contains benzene gas, wherein said device, comprising a combination of sensors, is disposed on a base substrate that includes: a) at least one multi- or single-wall carbon nanotube sensor functionalised with oxygen plasma and decorated with rhodium (Rh) clusters; b) at least one multi- or single-wall carbon nanotube sensor functionalised with oxygen plasma, the at least one sensor being one of undecorated or decorated with metal clusters selected from one of gold, palladium, nickel and titanium; and c) at least one multi- or single-wall carbon nanotube sensor functionalised with oxygen plasma and decorated with platinum (Pt) clusters; said base substrate further comprising interdigital metal electrodes for measuring a variation in a resistance of said sensors;
   measuring an electrical resistance of each one of the sensors comprised in the device; and
   wherein the variation of the electrical resistance of each one of the sensors comprised in the device facilitates analysis and determination of presence of benzene gas and quantification of a concentration of benzene gas; and if a new measurement is desired, desorbing the gases from the sensor by applying ultraviolet light or heat to the sensor.

7. The method according to claim 6, wherein the device is used in at least one of a chemical industry, a petrochemical industry, petrol stations, or household, aeronautical or research applications.

8. The device according to claim 1, wherein said device is re-useable for several measurements.

* * * * *